United States Patent [19]
Hirschl et al.

[11] Patent Number: 5,492,109
[45] Date of Patent: Feb. 20, 1996

[54] LIQUID VENTILATOR WITH VENTURI-INDUCING PATIENT CONNECTOR

[75] Inventors: Ronald B. Hirschl, Whitmore Lake; Jean P. Montoya; Scott I. Merz, both of Ann Arbor, all of Mich.

[73] Assignee: The Regents of the University of Michigan, Ann Arbor, Mich.

[21] Appl. No.: 147,057

[22] Filed: Nov. 3, 1993

[51] Int. Cl.$^6$ .............................. A62B 7/06; A62B 9/06; A61M 16/00
[52] U.S. Cl. .............................. 128/201.21; 128/204.25; 128/913; 128/207.14
[58] Field of Search .............................. 128/913, 201.21, 128/204.18, 207.14, 911, 912, 204.25

[56] References Cited

U.S. PATENT DOCUMENTS

| | | | |
|---|---|---|---|
| 4,232,665 | 11/1980 | Vaseen | 128/913 |
| 4,867,153 | 9/1989 | Lorenzen et al. | 128/205.12 |
| 5,158,536 | 10/1992 | Sekins et al. | 604/20 |

FOREIGN PATENT DOCUMENTS

| | | | |
|---|---|---|---|
| 0858824 | 8/1981 | U.S.S.R. | 128/913 |
| WO9219232 | 11/1992 | WIPO. | |
| WO9309833 | 5/1993 | WIPO. | |

OTHER PUBLICATIONS

"A Mechanical Respirator for Control of Liquid Breathing", Moskowitz, pp. 1751–1752, Federation Proc, V29, #5, Sep./Oct. 1970
"Discussion of Liquid Breathing", Rahn, pp. 1753–1754, Federation Proceedings, V29, #5, Sep./Oct.–1970.
"Survival of Mammals . . . ", Clark Jr. et al, pp. 1755–1756, Science, vol. 152, Jun. 24, 1966.
"Required Properties of Liquids . . . ", Kylstra, pp. 1724, Federation Proceedings, V29, #5, Sep/Oct/–1970.
"Long–Term Survival of Dogs . . . ", Modell et al, pp. 1731–1736., V29,#5, Sep./ Oct.–1970.
"Experimental Pathology After Respiration . . . ", Gollan et al, pp. 249–262, Experimental Medicine & Surgery, V26, #4, Dec. 1968.
"Dogs Breathe Water", Scientific Newsletter, Apr. 6, 1965, V. 87, #15, p. 229.
"Perfusion of whole animals . . . heart–lung machine", Clark Jr. et al, pp. 1764–1770, Federation Proceedings, V.29, #5, Sep./Oct. 1970.
"Fluorocarbon Liquid Oxygenator", Dundas, pp. 1771–1777, Federation Proceedings, V.29, #5, Sep./Oct.–1970.
"Compliance and Diffusion . . . fluorocarbon fluid", Gollan et al, pp. 1725–1729, Federation Proceedings, V29, #5, Sep./Oct.–1970.
"Survival and histopathologic . . . liquid breathing," Patel et al, pp. 1740–1745, Federation Proceedings, V29, #5, Sep./Oct.–1970.
Oxygen Consumption & Carbon Dioxide Prod. During Liquid Ventilation–Hirschl–May 16, 1992, Univ of Michigan.

(List continued on next page.)

*Primary Examiner*—Kimberly L. Asher
*Attorney, Agent, or Firm*—Harness, Dickey & Pierce

[57] ABSTRACT

An involuntary respiratory apparatus for perfusing and entraining a breathable liquid from the lungs of a patient. The system includes a number of components which are interconnected by a conduit so as to form a substantially closed loop, single path circuit. The various components include a reservoir, a pump, an oxygenator, a heat exchanger, an endotracheal tube, a Y-connector, a valve and a controller. To simulate inspiration, the controller closes the valve, which is located downstream of the Y-connector, thereby forcing the liquid into the lungs of the patient. After a tidal volume of liquid has been perfused into the patient's lungs, the controller opens the valve. The Y-connector is shaped such that the flow of liquid through its inspiratory limb will cause the liquid in the patient's lungs to be entrained into the flow out of the Y-connector. In this manner, the Y-connector operates as an ejector pump and allows the apparatus to continuously perfuse the liquid through the single path circuit.

9 Claims, 2 Drawing Sheets

OTHER PUBLICATIONS

The American Physiological Society, pp. 2322–2323, Airway & Alveolar Pressures During Perfluorocarbon Breathing in Infant Lambs—Curtis—1990.

A New Experimental Approach for the Study of Cardiopulmonary Physiology During Early Development—Wolfson—1988, American Physiological Society, pp. 1436–1439.

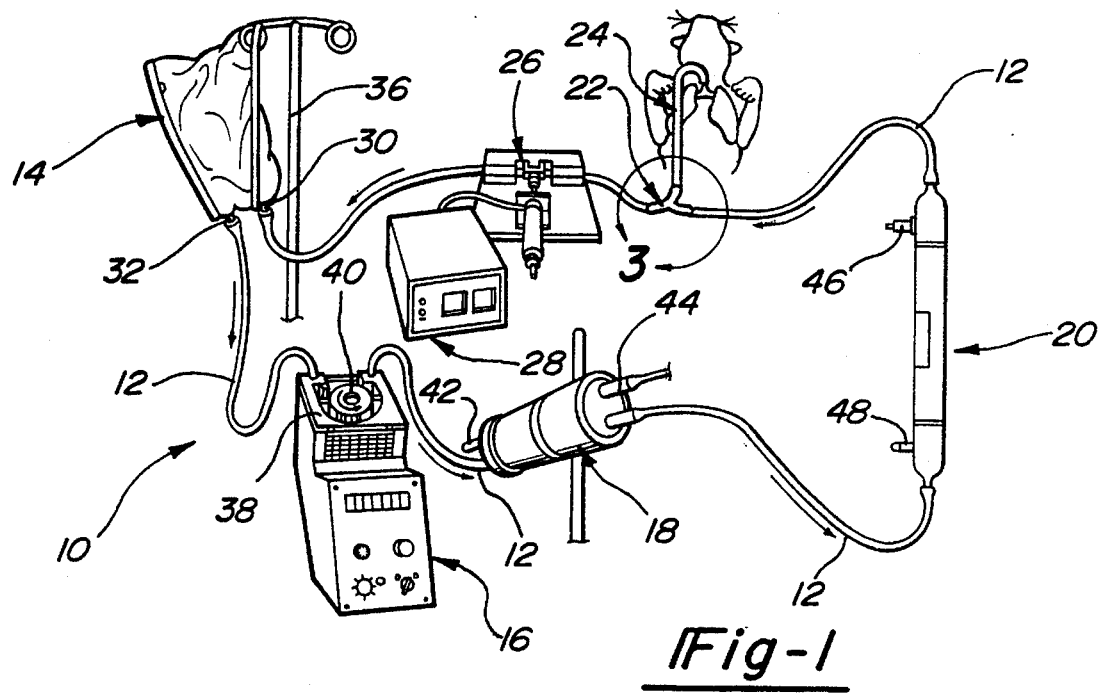
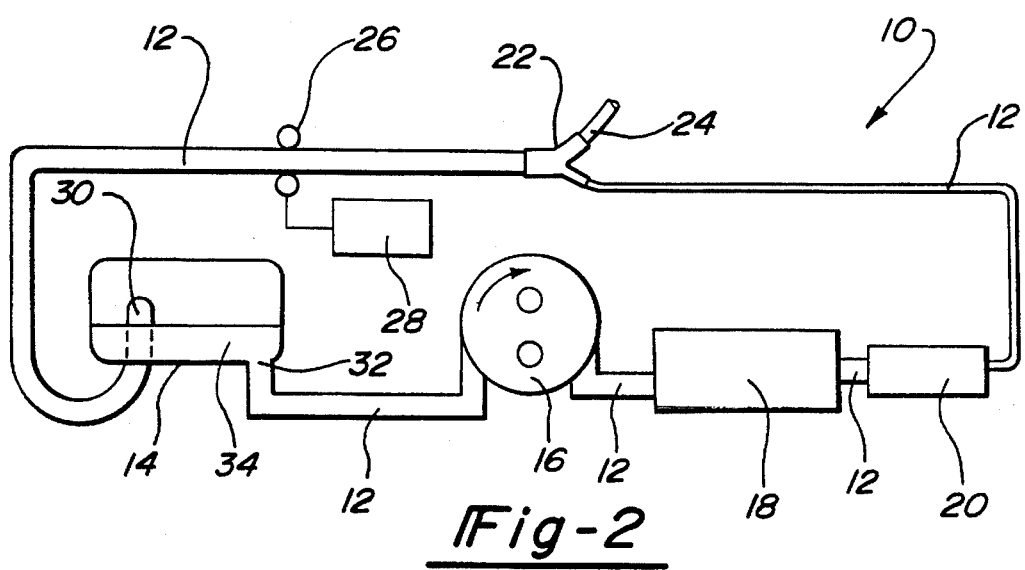

LIQUID VENTILATOR WITH VENTURI-INDUCING PATIENT CONNECTOR

BACKGROUND AND SUMMARY OF THE INVENTION

The present invention generally relates to pulmonary ventilation and, more particularly, to a pulmonary ventilator using a "breathable liquid".

As used herein, the phrase "breathable liquid" is meant to refer to liquids which are capable of delivering oxygen to, and removing carbon dioxide from, the pulmonary system or lungs of a patient. Examples of "breathable liquids" include, but are not limited to, saline, silicone, vegetable oils, perfluorochemicals and others. One of the presently preferred "breathable liquids" is perfluorocarbon liquid. Hereinafter, the phrase "perfluorocarbon liquid" is used in place of "breathable liquids". This use, however, is not intended to restrict the present invention specifically thereto.

Perfluorocarbon liquids, also known as perfluorocarbons or simply PFC's, are derived from common organic compounds in which fluorine atoms have replaced carbon bound hydrogen atoms. PFC's are colorless, odorless, non-flammable liquids which have a high dielectric strength and resistivity. They are substantially insoluble in water, are denser than water, exhibit low surface tensions, and have low viscosities. Perhaps the most unique characteristic of PFC's is their high affinity for gases, dissolving up to twenty times as much oxygen and over three times as much carbon dioxide as water. Like other materials which are widely used in the practice of medicine, PFC's are extremely biocompatible and non-toxic. In addition to liquid ventilation, perfluorocarbon liquids have found utility as artificial blood substitutes, in lung lavage (washing) and medical treatments such as convective lung hypothermia.

Pulmonary ventilation with various breathable liquids has been investigated from time to time during the last three decades and the ability to provide for adequate oxygenation and the elimination of carbon dioxide during liquid ventilation has been demonstrated. It was first demonstrated in the early 1960's that mammals could be submerged in hyperoxygenated saline, could breath the oxygenated liquid and could successfully resume gas breathing thereafter. Because of the practical difficulties involved with dissolving sufficient quantities of oxygen in saline (high pressures are required) and because the saline rinsed away much of the surfactant lining in the lung alveoli, the saline approach to liquid ventilation was eventually abandoned. These problems were overcome in the mid 1960's when PFC's were first used to support the respiration of various small animals. The biocompatibility and various other properties of certain PFC's has led to a significant body of ongoing research which appears to support promising clinical applications, including the treatment of Respiratory Distress Syndrome (RDS), Adult Respiratory Distress Syndrome (ADRS) and other situations where surfactant deficiencies in the lung compromise pulmonary functions.

To date, it has been clearly established that oxygenated perfluorocarbons can be used to provide total ventilation support over an extended period of time while enabling a return to gas breathing without long term side effects. The side effects which do result are typically minor and transient in nature (mild acidosis, lower blood $CO_2$, increased pulmonary vascular resistance and decreased lung compliance). Additionally, the various studies have also shown that PFC ventilation results in no adverse morphological, biochemical or histological effects.

In the United States, liquid ventilation has only been clinically studied in a few instances. Generally, these systems have been gravity systems where, during inspiration, oxygenated perfluorocarbon is placed into a reservoir and allowed to drain into the patient's lungs under the influence of gravity. During expiration, another reservoir is placed below the level of the patient's lungs and the perfluorocarbon is allowed to drain from the lungs, again under the influence of gravity.

In the laboratory, complex liquid ventilation systems utilizing modern extracorporeal life support technology have been described and used. Specifically, these systems have required the use of multiple roller pumps and multiple fluid reservoirs in order to provide control over all the parameters of inspiration, expiration, oxygenation and carbon dioxide removal. These systems have also necessitated the use multiple loop or bypass circuits for the perfluorocarbon ensure adequate inspiration and expiration. The systems have also included, in addition to the bypass circuit, the use of multiple valves to properly direct the perfluorocarbon into the lungs during inspiration and through the bypass circuit during expiration. The multiple valve and bypass systems have typically included a valve located in the circuit both before and after the patient, on what are known as the inspiratory limbs and expiratory limbs of the circuit. The valves are manipulated during inspiration and expiration so that the perfluorocarbon is either directed into the lungs (during inspiration) or diverted through the bypass circuit.

As the above discussion reveals, these prior liquid ventilation systems are quite complex and, often, too cumbersome to make clinical application practical. The need for a simplified and reliable liquid ventilation system is therefore obvious.

In achieving its main objective, namely, providing positive pressure, tidal volume liquid ventilation, the present invention overcomes and substantially alleviates the problems associated with the known prior systems.

Another object of the present invention is to provide a liquid ventilator which reduces the mechanical complexity of a liquid ventilation system through the adoption of a more simplified design. A related object is to allow both inspiration and expiration while eliminating the need for a bypass circuit.

Still another object of this invention is to provide a liquid ventilation system in which the breathable liquid is continuously being moved or pumped through the system.

In achieving the above and other objects, the present invention provides a pulmonary ventilator in which the breathable liquid, preferably perfluorocarbon, is recirculated through a single, closed loop circuit while adequately providing for both inspiration and expiration. The circuit of the present invention generally contains the following components connected in series by a conduit: a reservoir, a pump, an oxygenator, a heat exchanger, a Y-connector, an endotracheal tube, a valve and a controller.

The conduit leads from the reservoir to a continuously operable pump which forces or drives the perfluorocarbon through the circuit. From the pump, the perfluorocarbon travels to the oxygenator where carbon dioxide is removed and the perfluorocarbon is oxygenated. The perfluorocarbon is transferred from the oxygenator to a heat exchanger where it is heated or cooled to the desired temperature. From the heat exchanger, the perfluorocarbon travels through the conduit to the inspiratory limb of the Y-connector. The other two limbs of the Y-connector are an expiratory limb and an endotracheal limb. The endotracheal limb is attached to the endotracheal tube which extends into the lungs of the patient. The expiratory limb is connected by the conduit to the valve mentioned above. From the valve, the conduit feeds the perfluorocarbon back into the reservoir.

During operation, to simulate inspiration by the patient, the controller causes the valve to close thereby forcing the oxygenated and heated perfluorocarbon being driven by the pump through the inspiratory limb of the Y-connector, out the endotracheal limb and tube into the lungs of the patient. After a tidal volume of perfluorocarbon has been pumped into the lungs, as determined by the flow rate of the perfluorocarbon, the controller opens the valve. The perfluorocarbon within the patient's lungs is then entrained from the lungs as a result of the Y-connector. The specific configuration of the Y-connector generates a venturi effect which enhances drainage of the perfluorocarbon from the lungs while allowing for continuous profusion of the perfluorocarbon through the circuit. Passing through the valve, the carbon dioxide laden perfluorocarbon is directed back into the reservoir where the ventilation process begins to repeat its cycle.

The present invention is advantageous in a clinical setting since it provides a simple, single circuit liquid ventilator which is capable of continuously perfusing the perfluorocarbon without the need for an additional bypass circuit or multiple valves. Since the present invention requires only one valve, improvements in terms of mechanical simplicity and safety are achieved. While continued laboratory studies of present liquid ventilation system are ongoing, the data so far generated has demonstrated marked improvements in pulmonary function and gas exchange when compared to gas ventilation in animals with severe respiratory failure. It is therefore anticipated that the present invention will play a significant role in providing positive, tidal volume liquid ventilation during the treatment of severe respiratory failure in a simple yet safe manner.

Additional benefits and advantages of the present invention will become apparent to those skilled in art to which this invention relates from the subsequent description of the preferred embodiments and the appended claims, taken in conjunction with the accompanying drawings.

BRIEF DESCRIPTION OF THE DRAWINGS

FIG. 1 is a diagrammatic illustration of a liquid ventilator incorporating the principles of the present invention;

FIG. 2 is a schematic illustration of a liquid ventilator embodying the principles of the present invention.

DETAILED DESCRIPTION Of THE PREFERRED EMBODIMENT

Figure 3:
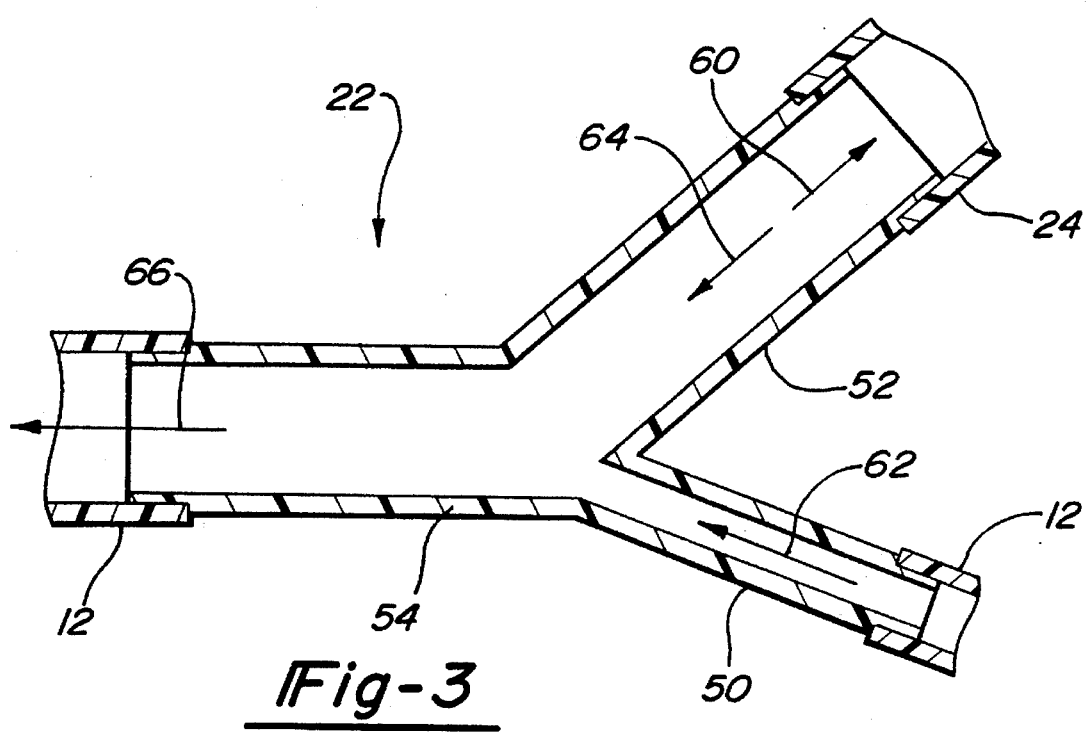
FIG. 3 is an enlarged sectional view of the Y-connector utilized with the present invention.

Referring now to the drawing, an apparatus for performing pulmonary ventilation according to the principles of the present invention is illustrated in FIG. 1 and designated at 10. The system 10 of the present invention is also schematically illustrated in FIG. 2. As is evident from the Figures, the system 10 incorporates a substantially closed loop, single path, unidirectional flow circuit.

The principal components of the present invention are connected, in series, by lengths of a conduit 12 formed from surgical grade tubing. The principal components include a reservoir 14; a pump 16; an oxygenator 18; a heat exchanger 20; a Y-connector 22; an endotracheal tube 24; a valve 26 and a controller 28.

The reservoir 14, which is capable of being acted upon by gravity, is generally defined by a rigid or flexible bag (flexible in the illustrated embodiment) and includes an inlet opening defined by an inlet fitting 30 and an outlet opening defined by an outlet fitting 32. As best seen in FIG. 2, the inlet fitting 30 enters from the bottom of the reservoir 14, but extends to a position located above the level of perfluorocarbon, generally designated at 34, contained therein. The outlet fitting 32 also extends from the bottom of the reservoir 14, but is positioned so that its outlet opening generally corresponds with the bottom or lowermost portion of the reservoir bag 14, below the level of the perfluorocarbon 34.

The reservoir 14 is supported by a rack or frame 36 which can be raised or lowered in height. This configuration of the reservoir 14, with the height being adjustable, allows the end-expiratory pressure of the perfluorocarbon 34 to be controlled by altering the height of the reservoir 14 in relation to the height of the endotracheal tube 24 and the patient.

The outlet fitting 32 of the reservoir 14 is connected by the conduit 12 to the pump 16. The pump 16 is a peristaltic pump which may be of an occlusive roller, centrifugal, linear or other well known variety. An occlusive roller pump 16 is generally illustrated in the Figures. The conduit 12 is fed through the pump 16 so that a portion of its length lies generally within a raceway 38 formed thereon. Rollers (not shown) are supported by a rotatable carrier 40 and are caused to engage and move along the length of the tubing 12 within the raceway 38 as the carrier 40 rotates. When used with the present invention, the pump 16 operates in a continuous manner and at a predetermined flow rate. The flow rate is chosen so that the desired inspiratory and expiratory tidal volume is produced in the patient. Leaving the pump 16, the conduit 12 feeds the perfluorocarbon 34 to the oxygenator 18.

The oxygenator 18 is the means by which carbon dioxide is removed from the perfluorocarbon 34 and replaced with oxygen. The oxygenator 18 can be any one of a number of well known varieties, such as a membrane lung or bubble oxygenator. For this reason, the specifics of the oxygenator are not more fully described herein. To maximize oxygenation of the perfluorocarbon 34, it is anticipated that 100% oxygen will need to be fed into the oxygenator 18 through a oxygen inlet 42 a rate corresponding to the flow of perfluorocarbon 34. Obviously, the specific rate at which the oxygen is supplied will also depend on numerous other factors including the flow rate of the perfluorocarbon 34. The displaced carbon dioxide is transported with excess oxygen and other gases out of the oxygenator 18 through a similar fitting or outlet 44.

From the oxygenator 18, the conduit 12 directs the perfluorocarbon 34 to the heat exchanger 20 or other means for controlling the temperature of the perfluorocarbon 34. The illustrated heat exchanger 20 is also of a well known variety, such as a water bath heat exchanger. In this type of heat exchanger 20, the perfluorocarbon 34 passes through a central conduit of the heat exchanger 20 and is heated to the predetermined temperature by water which is circulated through the heat exchanger 20 around the perfluorocarbon 34 conduit. As seen in FIG. 1, the water enters a water inlet 46 and exits through a water outlet 48 after having heated the perfluorocarbon liquid 34 to the desired temperature.

The conduit 12 leading from the heat exchanger 20 is connected to an inspiratory limb 50 of the Y-connector 22.

As seen in FIG. 3, the Y-connector 22 includes, in addition to the inspiratory limb 50, an endotracheal limb 52 and an expiratory limb 54. For reasons which will become more apparent from the discussion which follows, the inspiratory limb 50 has a diameter which is less than that of both the endotracheal limb 52 and expiratory limb 54, which are similar in size to each other.

With the conduit 12 attached to the expiratory limb 54 (the valve 26 being positioned downstream thereof) and with the endotracheal limb 52 being connected by the endotracheal tube 24 to the lungs of the patient 56 (generally designated as a cat in FIG. 1), involuntary inspiration in the patient 56 is induced as the valve 26 is closed. The valve 26 is a well known variety such as a pinch valve as illustrated. The valve 26 is closed by the controller 28 through the actuation of a cylinder 58 or another type of actuator. With the valve 26 closed, the flow of perfluorocarbon 34 generated by the continuously operating pump 16 travels, as designated by arrow 60, through the endotracheal limb 52 and the endotracheal tube 24 into the lungs of the patient 56. The endotracheal tube 24 itself is generally an off-the-shelf item designed so as to reduce resistance to liquid flow and, therefore, the pressure required to drive the liquid flow. Basically, the endotracheal tube 24 is a plastic, flexible tube that is inserted down the trachea of the patient 56.

Based on the flow rate of perfluorocarbon 34 produced by the pump 16, the controller 28, which is also an item that is commonly known within the industry, is programmed to maintain the valve 26 in its closed position until the desired inspiratory tidal volume of perfluorocarbon 34 has been generated within the patient 56. To simulate expiration, the controller 28, through the actuator 58, opens the valve 26 and the perfluorocarbon 34 within the patient 56 is entrained therefrom because of the specific configuration of the Y-connector 22. In the desired configuration, the Y-connector 22 operates as an ejector pump producing a venturi effect in the middle of the Y-connector 22 which enhances drainage and entrains perfluorocarbon 34 from the patient's lungs simulating expiration. This entrainment of the perfluorocarbon 34 by the flow through the inspiratory limb 50 allows for continuous perfusion of the perfluorocarbon 34 through the circuit of the apparatus 10 while achieving effective drainage of the patient's lungs.

More specifically, with the pinch clamp 26 closed, flow entering the inspiratory limb 50 is directed along arrow 60 by the occlusion of the conduit 12 downstream of the expiratory limb 54 into the endotracheal tube 24 and the lungs of the patient 56. During expiration, the velocity of the flow (arrow 62) entering the Y-connector 22 through the narrower inspiratory limb 50 is much higher than the velocity of the flow (arrow 64) out of the patient 56 and through the endotracheal limb 52. The momentum of the flow 62 (which is the product of the velocity and the mass flow rate) is also much higher. Therefore, if a momentum balance is performed on a controlled volume through the Y-connector 22, the net effects are a suction pressure generated in the endotracheal limb 52 and a positive pressure generated in the expiratory limb 54. In other words, the high velocity jet produced from the flow 62 through the inspiratory limb is accompanied by an entrained flow 64 from the endotracheal limb 52. To achieve this effect, the product of the velocity and mass flow rate at the inspiratory limb must be higher than the product of the velocity and mass flow rate at either the endotracheal limb 52 or the expiratory limb 54. For this reason, the diameter of the inspiratory limb 52 is much smaller than that of the endotracheal limb 52 and the expiratory limb 54. While their specific diameters will depend on numerous other design criteria of the system 10, it is believed that the inspiratory limb 50 will generally be about 0.375 inches in diameter while the expiratory and endotracheal limbs 54 and 52 will be about 0.5 inches in diameter. Obviously, the specific design criteria of the system 10 will dictate the exact dimensions of the various limbs 50, 52 and 54. The characteristics generated by the Y-connector 22 as an ejector pump are only important during expiration when the valve 26 is open.

From the valve 26, the conduit 12 directs the carbon dioxide laden perfluorocarbon 34 into the reservoir 14 completing the substantially closed circuit of the system 10.

As shown and described, the system 10 of the present invention provides a closed loop single circuit liquid ventilator which exhibits numerous benefits and advantages over prior systems. These benefits and advantages include, but are not limited to, providing a very simple single circuit ventilator having continuous perfusion of the perfluorocarbon 34 through the oxygenator 18 and heat exchanger 20 which improves the efficiency of the perfluorocarbon oxygenation and carbon dioxide removal without the need of an additional bypass circuit. By providing a single circuit system which utilizes a single valve which, from a mechanical point of view, offers significant improvements in terms of mechanical simplicity and safety; by preventing an interchange between the inspiratory, expiratory and endotracheal limbs so that the perfluorocarbon 34 is readily entrained thereby further enhancing drainage and allowing for continuous perfusion of perfluorocarbon 34 through the circuits; by providing the ability to adjust the height of the reservoir 14 thereby allowing manipulation end-expiratory pressure.

As an alternative embodiment, the system 10 could be provided with more than one Y-connector 22 with each successive Y-connector 22 being connected in parallel. The end result would be enhanced suction out of the endotracheal tube 24.

While the above description constitutes the preferred embodiment of the present invention, it will be appreciated that the invention is susceptible to modification, variation and change without departing from the proper scope and fair meaning of the accompanying claims.

We claim:

1. An involuntary respiratory apparatus for introducing and removing liquid from the lungs of a patient, said apparatus comprising:

a reservoir adapted for containing a liquid therein, said reservoir having an inlet opening to receive said liquid thereinto and an outlet opening for dispensing said liquid therefrom;

a substantially closed loop conduit means for transporting said liquid therethrough, said conduit means being coupled to said outlet opening for receiving said liquid from said reservoir and also being coupled to said inlet opening for discharging said liquid from said conduit means into said reservoir;

pump means for continuously perfusing said liquid through said conduit means;

oxygenation means for oxygenating said liquid;

temperature control means for maintaining the temperature of said liquid within a predetermined range of temperatures;

one endotracheal tube generally coupled to said conduit means and enabling said liquid to be both introduced into and withdrawn from said lungs of said patient through said one endotracheal tube; and inspiration and expiration means for causing the introduction of a predetermined volume of said liquid through said endotracheal tube into said lungs generally simulating inspiration by said patient and subsequently withdrawing a predetermined volume of said liquid from said lungs through said endotracheal tube generally simulating expiration by said patient, whereby said patient involuntarily respires as said liquid is introduced and withdrawn from said lungs, said inspiration and expiration means including a Y-connector having an inspiratory limb connected to said conduit means in an upstream direction, an expiratory limb connected to said conduit means in a downstream direction and an endotracheal limb connected to said endotracheal tube, said inspiration and expiration means further including means for selectively occluding and unoccluding said conduit means downstream of said Y-connector, and said inspiratory limb having a diameter sufficiently smaller than a diameter of said expiratory limb to form a venturi when said conduit means is unoccluded downstream of said Y-connector as liquid flows into said Y-connector through said inspiratory limb and from said Y-connector through said expiratory limb to draw liquid from said endotracheal tube and the lungs of the patient into said Y-connector, and when said conduit means is occluded, liquid pumped through said inspiratory limb into said Y-connector is directed out of said Y-connector through said endotracheal tube and into the lungs of the patient whereby alternating occlusion and unocclusion of said conduit means produces simulated inspiration and expiration of the patient.

2. The involuntary respiratory apparatus set forth in claim 1 wherein said conduit means forms a single path substantially closed loop.

3. The involuntary respiratory apparatus set forth in claim 1 wherein said conduit means is a tube interconnecting said reservoir, said pump means, said oxygenating means, said temperature control means, said endotracheal tube and said inspiration and expiration means.

4. The involuntary respiratory apparatus set forth in claim 1 wherein said reservoir, said pump means, said oxygenating means, said temperature control means, said endotracheal tube and said inspiration and expiration means are interconnected in series.

5. The involuntary respiratory apparatus set forth in claim 1 wherein said conduit means successively interconnects said reservoir to said pump means, said pump means to said oxygenating means, said oxygenating means to said temperature control means, said temperature control means to said inspiration and expiration means, and said inspiration and expiration to said reservoir.

6. The involuntary respiratory apparatus set forth in claim 1 wherein said means for selectively occluding and unoccluding said conduit means includes a valve and control means, said control means for causing said valve to occlude said conduit means causing said liquid to be introduced into said lungs of said patient.

7. The involuntary respiratory apparatus set forth in claim 6 wherein said valve is a pinch valve.

8. The involuntary respiratory apparatus set forth in claim 1 wherein said pump means is a peristaltic pump.

9. The involuntary respiratory apparatus set forth in claim 1 wherein said inspiratory limb has a diameter which is less than the diameter of said endotracheal limb.

* * * * *